US011918177B2

(12) United States Patent
Piponi (10) Patent No.: US 11,918,177 B2
(45) Date of Patent: Mar. 5, 2024

(54) DYNAMIC ILLUMINATION TO IDENTIFY TISSUE TYPE

(71) Applicant: Verily Life Sciences LLC, South San Francisco, CA (US)

(72) Inventor: Daniel Piponi, Oakland, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 680 days.

(21) Appl. No.: 16/587,469

(22) Filed: Sep. 30, 2019

(65) Prior Publication Data

US 2020/0107727 A1    Apr. 9, 2020

Related U.S. Application Data

(60) Provisional application No. 62/740,587, filed on Oct. 3, 2018.

(51) Int. Cl.
*A61B 1/00* (2006.01)
*A61B 1/06* (2006.01)
(Continued)

(52) U.S. Cl.
CPC .... *A61B 1/000094* (2022.02); *A61B 1/00006* (2013.01); *A61B 1/000096* (2022.02);
(Continued)

(58) Field of Classification Search
CPC .............. A61B 5/0084; A61B 1/00006; A61B 1/00009; A61B 1/0005; A61B 1/0638;
(Continued)

(56) References Cited

U.S. PATENT DOCUMENTS 9,717,417 B2    8/2017   DiMaio et al.
9,907,471 B2    3/2018   Caves et al.
(Continued)

FOREIGN PATENT DOCUMENTS

AU       2015204444 B2 *  9/2017  ......... A61B 1/00009
CA          2902771 A1 *  9/2014  ......... A61B 1/00059
(Continued)

OTHER PUBLICATIONS

Kalyan Kumar et al., (hereinafter Kumar) : "Discrimination of Normal and Malignant Stomach Mucosal Tissue by Raman Spectroscopy"; 0924-2031 © 2007 Elsevier B.V. (Year: 2007).*
(Continued)

*Primary Examiner* — Dramos Kalapodas
(74) *Attorney, Agent, or Firm* — CHRISTENSEN O'CONNOR JOHNSON KINDNESS PLLC (57) ABSTRACT

An imaging system includes a light source to emit a plurality of wavelengths of light, and a camera coupled to receive the light reflected back from tissue in a body. Also included are a database with reflectance data for a plurality of tissue types, and a controller coupled to the light source, the database, and the camera. The controller causes the imaging system to perform operations, including: generating image data with the camera; receiving the image data from the camera with the controller; comparing, with the controller, the image data to the reflectance data in the database; and determining a tissue type in the image data in response to comparing the image data to the reflectance data.

17 Claims, 4 Drawing Sheets

(51) Int. Cl.
*A61B 5/00* (2006.01)
*A61B 5/107* (2006.01)
*G06F 18/22* (2023.01)
*G06F 18/2415* (2023.01)
*G06V 10/141* (2022.01)
*G06V 10/143* (2022.01)
*G06V 10/56* (2022.01)
*G06V 10/60* (2022.01)
*G06V 10/74* (2022.01)
*H04N 23/74* (2023.01)
*H04N 23/50* (2023.01)

(52) U.S. Cl.
CPC .......... *A61B 1/0005* (2013.01); *A61B 1/0638* (2013.01); *A61B 1/0655* (2022.02); *A61B 5/0084* (2013.01); *A61B 5/1076* (2013.01); *A61B 5/7275* (2013.01); *G06F 18/22* (2023.01); *G06F 18/24155* (2023.01); *G06V 10/141* (2022.01); *G06V 10/143* (2022.01); *G06V 10/56* (2022.01); *G06V 10/60* (2022.01); *G06V 10/761* (2022.01); *H04N 23/74* (2023.01); *G06V 2201/03* (2022.01); *H04N 23/555* (2023.01)

(58) Field of Classification Search
CPC ... A61B 5/1076; A61B 5/7275; A61B 5/0075; A61B 5/0077; A61B 5/02007; A61B 5/0537; A61B 5/4041; A61B 90/361; A61B 2090/306; A61B 2090/309; A61B 2090/3614; A61B 2090/365; A61B 1/00057; A61B 1/000094; A61B 1/000096; G06K 9/6215; G06K 9/6278; H04N 5/2354; H04N 2005/2255; G06V 10/141; G06V 10/143; G06V 10/56; G06V 10/60; G06V 10/146; G06N 5/003; G06N 7/005

See application file for complete search history.

(56) References Cited

U.S. PATENT DOCUMENTS

| | | | |
|---|---|---|---|
| 2005/0047663 A1* | 3/2005 | Keenan | G06V 20/13 382/254 |
| 2006/0013454 A1 | 1/2006 | Flewelling et al. | |
| 2006/0241496 A1* | 10/2006 | Fengler | A61B 1/0638 600/476 |
| 2007/0031042 A1* | 2/2007 | Simental | G06V 20/13 382/191 |
| 2016/0110584 A1* | 4/2016 | Remiszewski | G06V 20/69 382/133 |
| 2018/0081179 A1* | 3/2018 | Samec | A61B 5/6803 |
| 2018/0247153 A1* | 8/2018 | Ganapati | G06F 18/285 |
| 2020/0085287 A1* | 3/2020 | Lawrenson | A61B 5/112 |
| 2020/0108066 A1* | 4/2020 | Goel | A61K 45/06 |

FOREIGN PATENT DOCUMENTS

| | | | | |
|---|---|---|---|---|
| CN | 105324063 B | * | 3/2018 | ........ A61B 1/00009 |
| CN | 108024695 B | * | 5/2021 | ........ A61B 1/00066 |
| EP | 2335555 A1 | * | 6/2011 | ........ A61B 1/00057 |
| EP | 3265822 B1 | * | 4/2021 | ............ A61B 1/041 |
| WO | 2018049215 A1 | | 3/2018 | |

OTHER PUBLICATIONS

Kumar et al., "Discrimination of normal and malignant stomach mucosal tissues by Raman spectroscopy: A Pilot Study", Vibrational Spectroscopy, Elsevier Sciences, Amsterdam, NL, vol. 44, No. 2., May 24, 2007, 6 pages.

International Search Report & Written Opinion dated Dec. 4, 2019 in corresponding International Patent Application No. PCT/US2019/053885, 14 pages.

* cited by examiner

DYNAMIC ILLUMINATION TO IDENTIFY TISSUE TYPE

CROSS-REFERENCE TO RELATED APPLICATIONS

This application claims the benefit of U.S. Application No. 62/740,587, filed on Oct. 3, 2018, the contents of which are incorporated herein by reference.

TECHNICAL FIELD

This disclosure relates generally to surgical technologies, and in particular, relates to illumination of surgical spaces.

BACKGROUND INFORMATION

During open surgery often it is difficult for surgeons to see the surgical area and accurately identify biological structures in the surgical area. This problem may be exacerbated when the surgical area is badly damaged (e.g., because of an accident, tumor growth, adhesion, or the like), or when the surgical area is poorly illuminated/partially obscured from sight. Additionally, the perceived color of anatomical features may change due to the various wavelengths emitted from various illumination sources (e.g., in some hospital settings a blackbody emission source, like an incandescent light, may be used during surgery, while in other hospitals an LED based light source with a blue-leaning emission spectrum may be used). Since the anatomical structures may appear to be different colors depending on the light source, identifying various organs and tissues may be complicated in certain environments.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an apparatus and method for illumination to identify tissue are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

During surgery, it is often important to identify specific tissue types and structures, where correct identification can make the difference between morbidity and patient risk and successful surgical outcomes. This problem is not easy since many tissue types appear similar or identical, or can otherwise be covered by fat or other connective tissue. As stated, this limits the surgeon's ability to correctly identify objects. The instant disclosure allows for the identification of different tissue types by a combination of specially adapted illumination and logic (which may be implemented in hardware, software, or a combination thereof).

In some embodiments, the system disclosed here includes an illuminator that uses a small number of light sources (e.g., LEDs, lasers, or a filtered broadband source) at specially selected wavelengths, and an image sensor sensitive to those wavelengths used to view the surgical field. Logic can use the image(s) captured by the image sensor to determine the tissue type. An important feature is the method by which the wavelengths are selected so as to be optimal for the task.

When biological tissues are observed using N wavelengths, each pixel in the resulting image can be described by N numbers corresponding to the intensity at each wavelength—for some cameras we have N=3 corresponding to red, green, and blue. Each pixel can be thought of as a point in an N-dimensional space. It is observed that for many tissue types, although the points for pixels in the same tissue can vary over the sample because of non-homogeneity of the tissue and variations in lighting angle, for each tissue type they tend to cluster into approximately ellipsoid regions in the N-dimensional space. This clustering can be even more robust when the variables used to form the N-dimensional space correspond to either diffuse spectral reflectance (which is independent of lighting angle) or ratios of reflected light intensity. Since points in a given cluster are independent and identically distributed, it is possible to model these points as belonging to an N-dimensional normal distribution. Given such probability distributions for pixels from each tissue type, the system can use Bayes' theorem to deduce the probability that a newly observed pixel belongs to each tissue type. The system then chooses the most likely type. In practice, this requires computing the means and covariance for each tissue type based on a training set (for which ground truth is available as determined by a person with suitable anatomic knowledge). For a new pixel the system wishes to identify, it may find the cluster that is "closest" using the Mahalanobis distance which takes into account that each cluster has a different covariance.

The approach of picking the most likely cluster could include using the "naive Bayes" method. One point of novelty in the approach proposed here is that the system may choose a small set of wavelengths to illuminate the surgical field and uses an optimization method to select the best set of wavelengths. "Best" here means the set that results in the Bayes method performing accurately on a test set of pixels for which we know the ground truth. It is appreciated that, in some embodiments, there are many alternative approaches that could be taken other than using a native Bayes approach—for example one could take a decision tree based approach.

This is potentially a complex optimization problem: the system wants to optimize the outcome of an algorithm that depends on wavelength choices. There may be a discrete set of wavelengths at the system's disposal. And the measured outcome counts the number of correct results on a test set. Both of these quantities are discrete, not continuous, so the system may not directly use a calculus based approach to optimize. The discrete variables could be approximated with continuous ones, but even then there may be many local minima so there is no guarantee that the best performing set of wavelengths has been found. This means there may be a combinatorial search. Suppose the system employs four illumination wavelengths and we have 400 choices for each light source. This is 400*399*398*387/(1*2*3*4) which is more than a billion combinations, each of which requires testing on thousands of pixels—so trillions of individual predictions for pixels need to be made.

However, in some embodiments, by implementing the naive Bayes algorithm on a GPU (graphics processing unit) instead of the CPU, we are able to test hundreds or thousands of wavelength combinations simultaneously. This makes it possible to find the best combination for realistic data sets in a reasonable time.

Additionally, this approach is flexible in the type of illuminators it can work with. For example, if the system is configurable with 400 different LED types, for example, and each LED type has a different bandwidth and spectrum, we can still use the same method. The system needs to know how the training samples look when illuminated by each LED type. For this, the system can either illuminate the samples with the LED types, or use a benchtop multispectral imager to simulate how each sample would look with each LED. The system can then perform the algorithm with the 400 images. Note that in this case there is a strong advantage to using a combinatorial search because there may not be an optimizable formula for the spectra of a collection of LEDs.

It is appreciated that the system can be designed with optimal illuminator sets for particular tissue discrimination problems. For example, if the user of the system was interested in distinguishing between a number of different nerve and blood vessel types then the user would choose illuminators best adapted to this task.

The following disclosure will describe the embodiments discussed above, in addition to other embodiments, as they relate to the figures.

Figure 1:
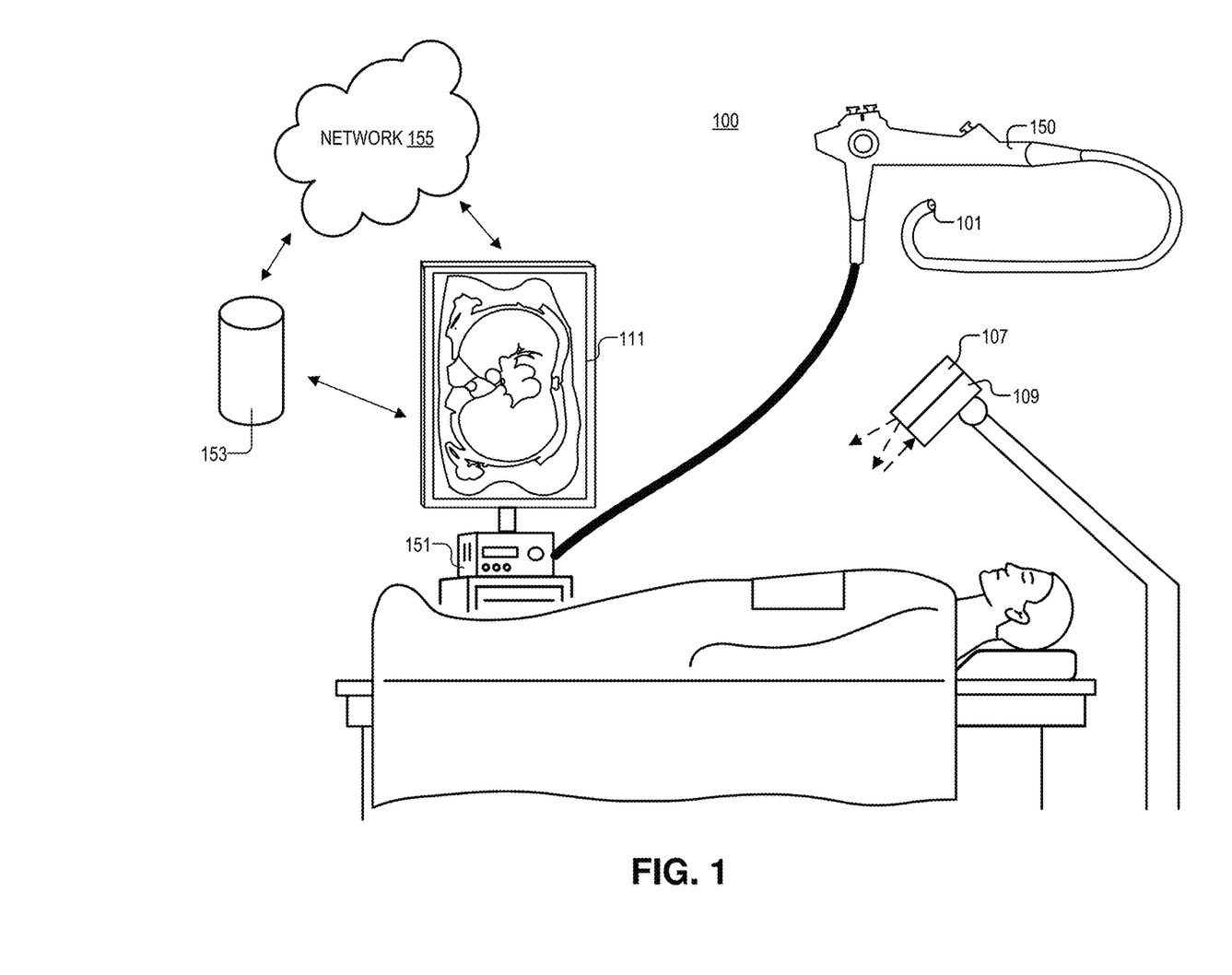
FIG. 1 illustrates an imaging system, in accordance with an embodiment of the present disclosure.

FIG. 1 illustrates an imaging system 100, in accordance with an embodiment of the present disclosure. Imaging system 100 includes endoscope 150 (with distal tip 101), light source 107, and camera 109, display 111, computer 151, storage 153, and network 155. It is appreciated that the controller of system 100 may include elements of computer 151, storage 153, and network 155 as well as control circuitry and software contained in local devices. Put another way, the controller may be a distributed system where different processes occur in different locations (e.g., in endoscope 150, in computer 151, and/or on remote servers), in accordance with the teachings of the present disclosure. As shown, all components depicted are coupled by wires or wirelessly.

In the depicted embodiment, imaging system 100 includes light source 107 (which may include one or more light emitters, e.g., diodes, lasers, etc.) and camera 109. Light source 107 may emit a plurality of wavelengths of light, and camera 109 may receive the light reflected back from tissue in the body. A database (e.g., contained in storage 153, or in any of the devices depicted) includes reflectance data for a plurality of tissue types in the body. A controller is coupled to light source 107, the database, and camera 109, and the controller includes logic that when executed by the controller causes the imaging system to perform operations. For example, operations may include receiving the light reflected back from the tissue with camera 109, generating image data with camera 109, and receiving the image data from the camera 109 with the controller. As described above, the controller may compare the image data to the reflectance data in the database, and determine a tissue type in the image data in response to comparing the image data to the reflectance data. For example, determining a tissue type may include calculating a distance in an N dimensional color space between reflectance data points (e.g., individual pixels) in the reflectance data, and image data points (e.g., individual pixels) in the image data. In some embodiments, the controller may further determine a probability that the image data includes a specific tissue type (e.g., nerve, skin, bone etc.) using Bayes theorem.

In some embodiments, determining the tissue type may include calculating a distance in a color space (e.g., N dimensional space, where N is the number of discrete light emitters in the light source) between reflectance data points in the reflectance data and image data points in the image data. In some embodiments, the distance is the Mahalanobis distance from a cluster of the reflectance data points.

In some embodiments, the wavelengths of light that light source 107 can emit are preselected and pre-optimized (e.g., before the surgery). However, in other embodiments the wavelengths, and the specific light emitters (e.g., the specific diode) in the light source that produce the light, are optimized during the surgical procedure. Put another way, the plurality of wavelengths of light emitted from the light source 107 may change dynamically from a first emission profile to a second emission profile. In one embodiment, the dynamic emission profile changes may be optimized for contrast by dynamic adjusts (e.g., over a few seconds) to the illumination. The dynamic changes may be executed in a transformed domain as opposed to the image space. In yet another example, the first emission profile may include three light emitters emitting 400 nm light, 530 nm light, and 700 nm light, and the second emission profile may include the three light emitters emitting 420 nm light, 535 nm light, and 680 nm light. This may be in response to the user inputting a specific tissue type to identify in the image data. For example, the user/surgeon may be looking at a portion of the body which contains both muscle and nerve tissue. Accordingly, the user may specify for the system to change the light emission parameters to better show/identify the nerve tissue. Changing the illumination profile may change the calculated probability that the image data includes the specific tissue type. For example, the calculated probability may be higher using the image data generated from the second emission profile than using the image data generated from the first emission profile (or vice versa). In some embodiments, the system may change the emission profile automatically if the system is not identifying tissue with a threshold degree of confidence (e.g., below 70% confidence of a tissue type). In one embodiment, if the system indicates that the tissue under inspection has substantially equal probabilities (e.g., within a threshold range) of being different tissue types (e.g., 40% probability of being a nerve and 41% probability of being fat), then the system may automatically, or provide the user an option to, change illumination wavelengths to improve disambiguation between the identified tissue possibilities.

As stated above, it is appreciated that changing the plurality of wavelengths from light source 107 from the first emission profile to the second emission profile may include searching a spectrum of wavelengths to arrive at the second emission profile. In some embodiments, the search calculations may be performed using a graphics processing unit (GPU) contained in the controller.

As shown, display 111 is coupled to the controller. Display 111 receives augmented image data derived from the image data, and the augmented image data indicates the tissue type. Display 111 can then show, in real time, an augmented image indicating (e.g., with color, word/number labels, or the like) the tissue type.

In some embodiments, network 155 and storage 153 may run algorithms and perform image processing. Computer 151 may also handle some amount of image processing, communicate with storage 153/network 155, and control various operational aspects of endoscope 150 (e.g., the amount of light output from distal tip 101, contrast of the image received from the camera, or the like).

In some embodiments (that will be described later), endoscope 150 may include the light emitters and the camera to perform the imaging. In the depicted embodiment, the proximal (hand-held) end of endoscope may have a number of buttons and joysticks to control the movement of distal tip 101. One of ordinary skill in the art will appreciate that endo scope 150 depicted here is merely a cartoon illustration of an endoscope, and that the term "endoscopy" should encompass all types of endoscopy (e.g., laparoscopy, endoscopy, robotic surgery, or any other situation when a camera is inserted into a body), and that an endoscope should include at least "chip-on-a-tip" devices, rod lens devices (ridged), or image fiber devices (flexible), to name a few. Endoscope 150 may be included in surgical robotic systems or coupled to a surgical robot.

Figure 2:
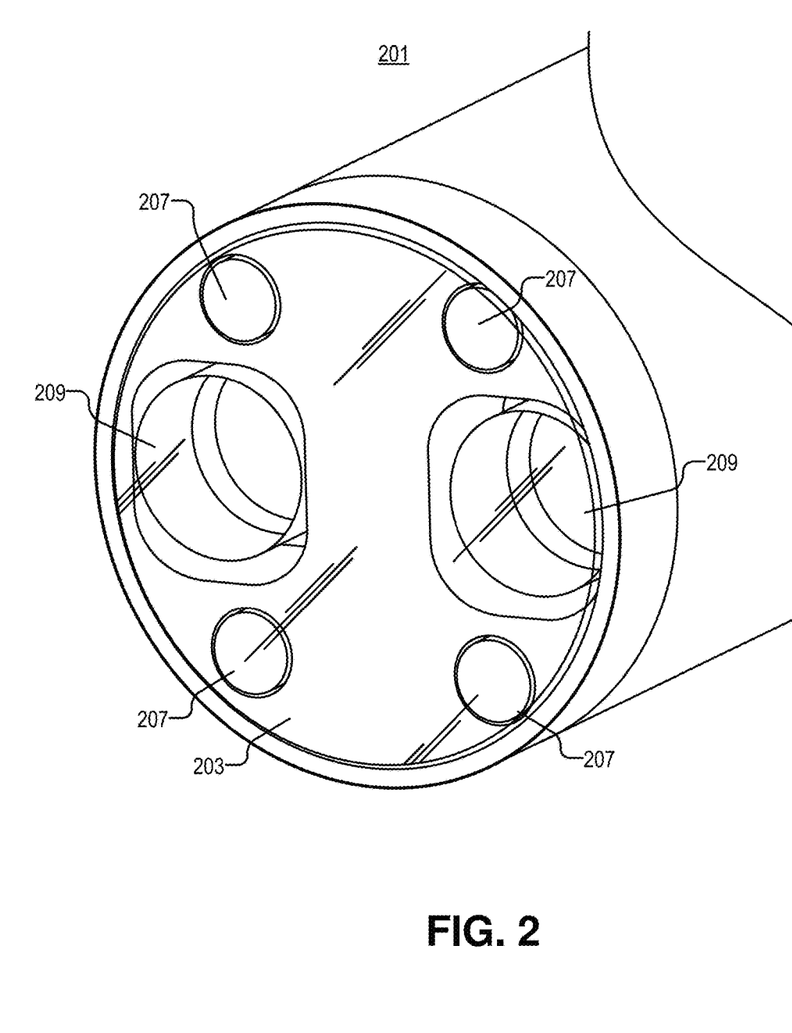
FIG. 2 illustrates a distal tip of the endoscope depicted in FIG. 1, in accordance with an embodiment of the present disclosure.

FIG. 2A illustrates the distal end 201 of the endoscope tube depicted in FIG. 1, in accordance with an embodiment of the present disclosure. It is appreciated that in the depicted embodiment, camera 209 (e.g., similar to camera 109) and light source 207 (e.g., similar to light source 107) are disposed within an endoscope, and light source 207 and camera 209 are positioned to emit the light and receive the light, respectively, through distal end 201 of the endoscope. As illustrated, light source 207 (e.g., light emitting diodes, laser diodes, the ends of optical fiber(s) to transmit light from a remote source) is coupled to emit light, and lens 203 (e.g., which may, or may not, have optical power and include sapphire, glass, or the like) is disposed proximate to distal tip 201 of the endoscope.

As shown, distal end 201 includes at least one camera 209 (e.g., image sensors, or fiber optics to send the image back to a camera in the proximal end of the endoscope) optically coupled to receive image light (e.g., light from the body/patient) through lens 203. Once the image light is received, cameras 209 may convert the image light into image data, and send the image data to the controller. In the depicted example, two cameras 209 are present in the endoscope (e.g., for stereo viewing), but in other examples a single camera may be employed to generate image data. As shown, lens 203 may form a seal with the housing of the endoscope tube (e.g., including electronic connections, fiber optic cables, actuators, or the like) to prevent moisture from reaching the electronic and optical components disposed behind lens 203.

Figure 3:
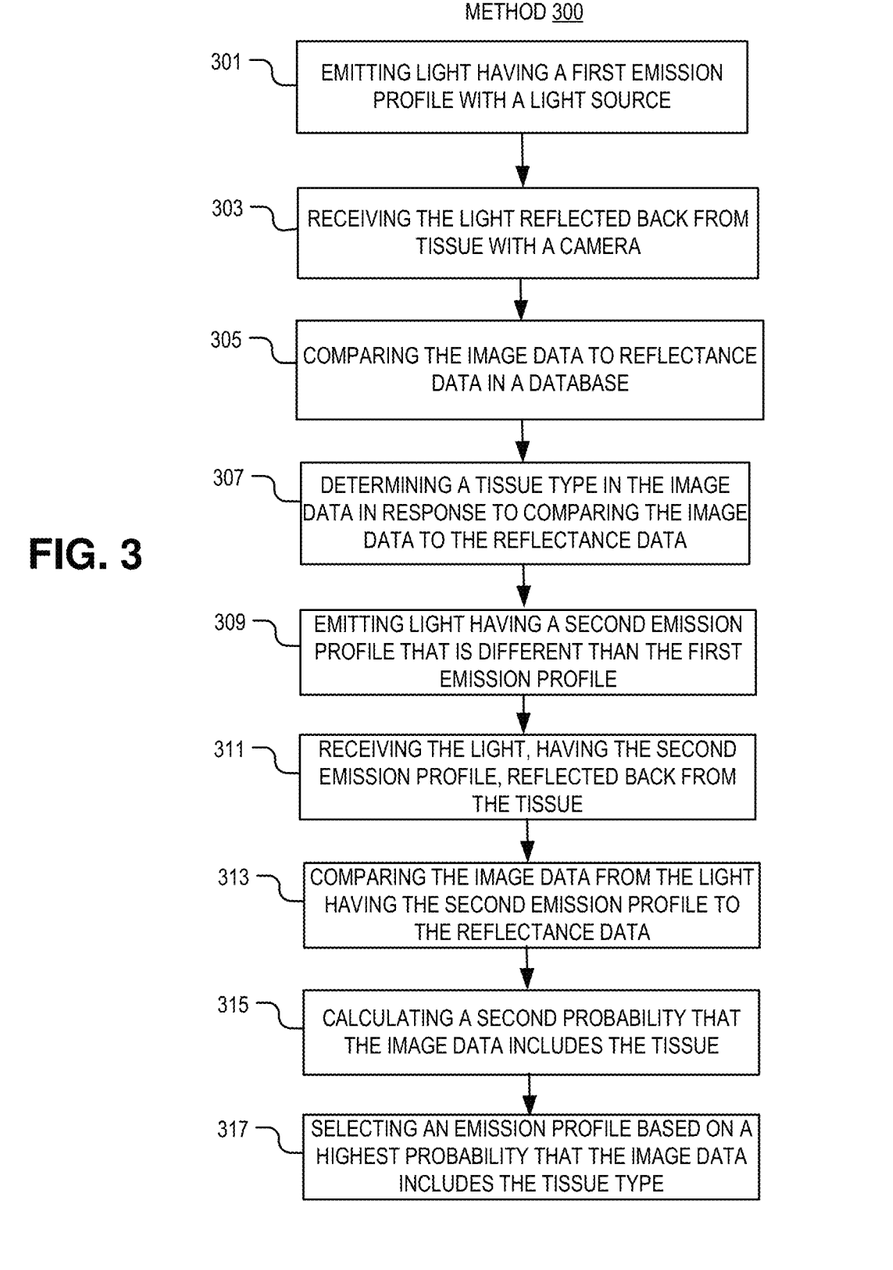
FIG. 3 illustrates a method of determining a tissue type, in accordance with an embodiment of the present disclosure.

FIG. 3 illustrates a method 300 of determining a tissue type, in accordance with an embodiment of the disclosure. One of ordinary skill in the art having the benefit of the present disclosure will appreciate that the order of blocks (301-317) in method 300 may occur in any order or even in parallel. Moreover, blocks may be added to, or removed from, method 300 in accordance with the teachings of the present disclosure.

Block 301 shows emitting light having a first emission profile with a light source including one or more light emitters. In some embodiments, light may be emitted from the distal end of an endoscope or other medical imaging equipment.

Block 303 illustrates receiving the light reflected back from tissue with a camera and outputting image data from the camera to a controller. In some embodiments the light may be received by a camera in the distal end of an endoscope or other medical imaging equipment.

Block 305 shows comparing the image data to reflectance data in a database using the controller coupled to the camera and the database. In some embodiments, comparing the image data to reflectance data includes calculating a distance (e.g., the Mahalanobis distance) in a color space between a cluster of reflectance data points (e.g., pixels) in the reflectance data and image data points in the image data (e.g., pixels). It should be appreciated that the database of reflectance data may be dynamically built/adjusted with use over the course of a given procedure. For example, as a procedure progresses the database of reflectance values may be updated based upon previous image frames from the procedure.

Block 307 shows determining a tissue type in the image data in response to comparing the image data to the reflectance data. In some embodiments, determining the tissue type includes calculating (e.g., using Bayes' theorem) a first probability that the image data includes the tissue type.

Block 309 illustrates emitting light having a second emission profile that is different than the first emission profile. The emission profile may change if the user would like to look for specific types of tissue that are best identified under a different illumination profile (different wavelengths of light). The illumination profile may include visible, infrared, or ultraviolet light. The system may receive the user's preferences through a user interface like a touch screen, keyboard, or the like. In some embodiments, the system may be able to automatically detect the anatomical structures being examined, and adjust the light source automatically to achieve higher confidence of proper identification.

Block 311 describes receiving the light, having the second emission profile (e.g., different wavelengths/duty cycles/intensities of light than the first emission profile), reflected back from the tissue with the camera (e.g., a CMOS image sensor or the like).

Block 313 shows comparing the image data from the light having the second emission profile to the reflectance data in the database. In some embodiments, the reflectance data in the database may be actual data points collected with different wavelengths or illuminations, or ellipsoid models in the N dimensional color space built from collected and/or theoretically calculated data points.

Block 315 shows calculating a second probability that the image data includes the tissue.

Block 317 illustrates comparing the first probability and the second probability, and selecting an emission profile based on the highest probability that the image data includes the tissue type. In some embodiments, this method can be repeated for multiple configurations of emission profiles (e.g., searching a spectrum of wavelengths) to arrive at the second, third, fourth, etc., emission profile. And the emission profile that results in the highest probability for accurate detection of anatomical features/tissue is used.

Figure 4:
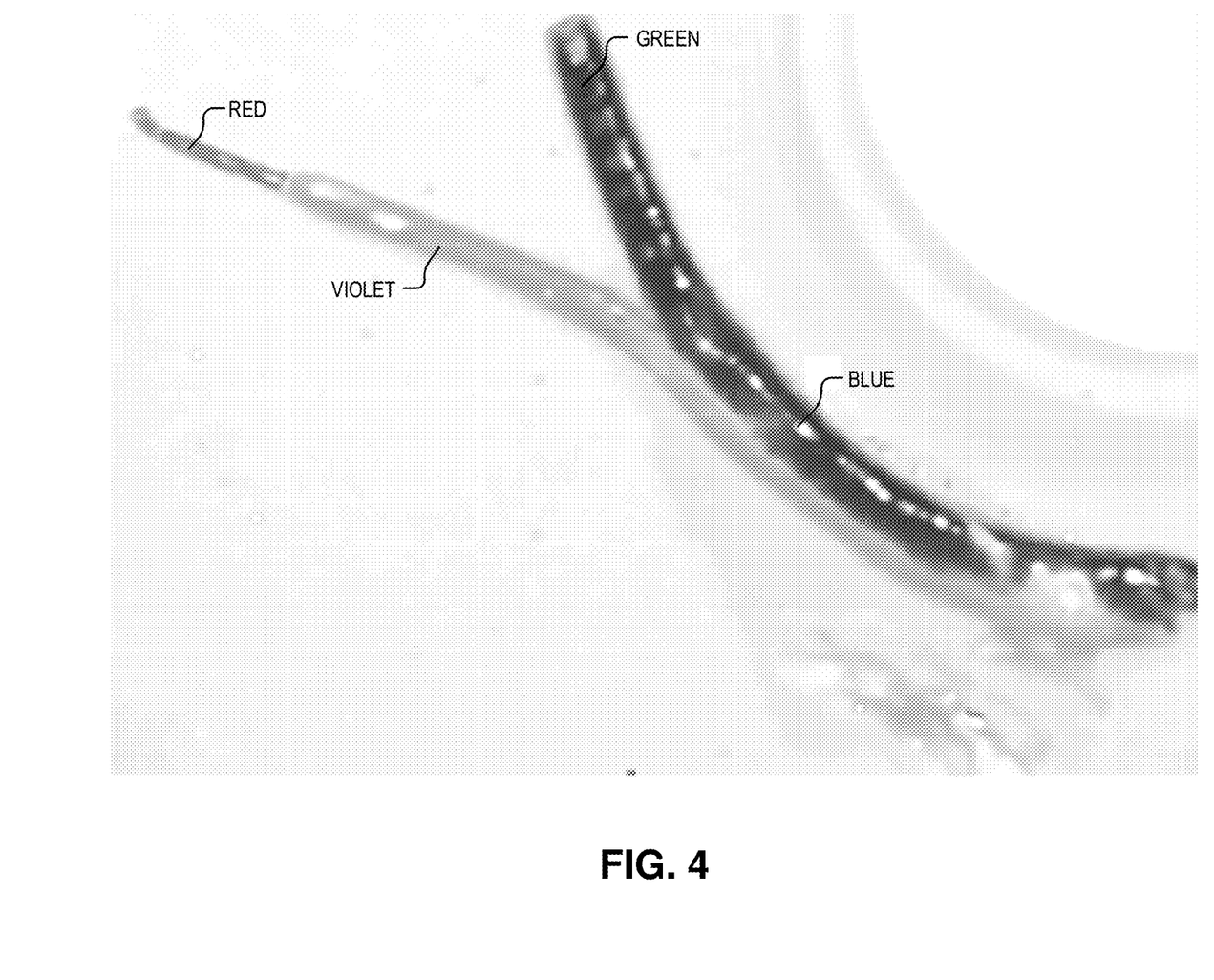
FIG. 4 illustrates displaying an augmented image, in accordance with an embodiment of the present disclosure.

As shown in FIGS. 1 and 4, after an optimized emission profile is chosen (e.g., with a high probability of detection) an augmented image or video feed may be sent to a display. The augmented image may indicate the anatomical structures.

FIG. 4 illustrates displaying an augmented image (which is reproduced in grayscale), in accordance with an embodiment of the present disclosure. The sample depicted consisted of two distinct nerves side by side. The ends of the nerves had the outer layers removed to expose the inside of the nerves. This example was exposed to three wavelengths in the infrared (1030 nm, 1214 nm, 1348 nm). As shown, the system here was able to differentiate the outer layer and exposed inside of the nerves, and create augmented image data where the system applied different colors to the outer layer and inside of the nerves. Specifically, one nerve is violet with red highlighting the exposed inside. The other nerve is blue with green highlighting the exposed inside. A system using this image augmentation technique may simulate fluorescent dyes, injected into patients for contrast, without the additional step of injecting patients. In some embodiments, the augmented fluorescent image depicted here could be displayed superimposed over the visible wavelength image.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging system, comprising:
   a light source including one or more light emitters to emit a plurality of wavelengths of light;
   a camera coupled to receive the light reflected back from tissue in or on a body;
   a database including reflectance data for a plurality of tissue types of the body; and
   a controller coupled to the light source, the database, and the camera, wherein the controller includes logic that when executed by the controller causes the imaging system to perform operations, including:
      in response to the camera receiving the light reflected back from the tissue, generating image data with the camera;
      receiving the image data from the camera with the controller;
      comparing, with the controller, the image data to the reflectance data in the database;
      determining a tissue type in the image data in response to comparing the image data to the reflectance data, wherein determining the tissue type includes calculating a probability that the image data includes the tissue type using the image data and the reflectance data;
      changing the plurality of wavelengths of light emitted from the light source from a first emission profile to a second emission profile based upon a probability threshold of tissue identification;
      combinatorially searching through multiple different emission profiles to select one of the multiple different emission profiles that provides a highest identification probability; and
      using the selected one of the multiple different emission profiles to identify the tissue type.

2. The imaging system of claim 1, wherein the camera and the light source are disposed within an endoscope, and wherein the light source and the camera are positioned to emit the light and receive the light, respectively, at a distal end of the endoscope.

3. The imaging system of claim 1, wherein comparing the image data to the reflectance data includes calculating a distance in a color space between reflectance data points in the reflectance data and image data points in the image data.

4. The imaging system of claim 3, wherein the distance is a Mahalanobis distance from a cluster of the reflectance data points.

5. The imaging system of claim 1, wherein determining the tissue type includes
   calculating a probability that the image data includes the tissue type using the image data and the reflectance data.

6. The imaging system of claim 5, wherein the controller further includes logic that when executed by the controller causes the imaging system to perform operations, including:
   preselecting a first emission profile for the plurality of wavelengths of light emitted from the light source based upon a selected surgical procedure or a specific tissue type expected to be encountered during the selected surgical procedure.

7. The imaging system of claim 5, wherein changing the plurality of wavelengths emitted from the light source from the first emission profile to the second emission profile includes searching a spectrum of wavelengths to arrive at the second emission profile.

8. The imaging system of claim 7, wherein the controller includes a graphics processing unit, and wherein the searching is performed on the graphics processing unit.

9. The imaging system of claim 1, further comprising a display coupled to the controller to receive augmented image data derived from the image data, wherein the augmented image data indicates the tissue type; and
  wherein the controller further includes logic that when executed by the controller causes the imaging system to perform operations, including:
  displaying an augmented image on the display indicating the tissue type.

10. A method of determining a tissue type, comprising:
  emitting light having a first emission profile with a light source including one or more light emitters;
  receiving the light reflected back from tissue in a body with a camera;
  outputting image data from the camera to a controller;
  comparing the image data to reflectance data in a database using the controller coupled to the camera and the database;
  determining a tissue type in the image data in response to comparing the image data to the reflectance data, wherein determining the tissue type includes calculating a first identification probability that the image data includes the tissue type using the image data and the reflectance data;
  changing the light emitted from the light source from the first emission profile to a second emission profile based upon a probability threshold of tissue identification;
  combinatorially searching through multiple different emission profiles, including the first and second emission profiles, to select one of the multiple different emission profiles that provides a highest identification probability; and
  using the selected one of the multiple different emission profiles to identify the tissue type.

11. The method of claim 10, wherein emitting the light includes emitting the light from a distal end of an endoscope, and wherein receiving the light includes receiving the light through the distal end of the endoscope.

12. The method of claim 10, wherein comparing the image data to reflectance data includes calculating a distance in a color space between reflectance data points in the reflectance data and image data points in the image data.

13. The method of claim 12, wherein the distance is the Mahalanobis distance from a cluster of the reflectance data points.

14. The method of claim 10, wherein calculating the first probability includes using Bayes' theorem.

15. The method of claim 10, wherein iteratively searching includes using a graphics processing unit included in the controller to calculate identification probabilities, including the first identification probability, associated with the multiple different emission profiles.

16. The method of claim 10, further comprising displaying an augmented image on a display, wherein the controller is coupled to receive augmented image data derived from the image data, and wherein the augmented image data indicates the tissue type.

17. The imaging system of claim 1, wherein changing the plurality of wavelengths of light emitted from the light source from a first emission profile to a second emission profile comprises:
  changing the plurality of wavelengths of light emitted from the light source from the first emission profile to the second emission profile in response to the tissue being identified as multiple different tissue types with substantially equal probabilities within a threshold range to improve disambiguation between the multiple different tissue types.

* * * * *